United States Patent [19]

Homann

[11] Patent Number: 4,574,157

[45] Date of Patent: Mar. 4, 1986

[54] PROCESS FOR PREPARING ANHYDROUS CYCLIC IMIDO ESTERS

[75] Inventor: Walter K. Homann, Dülmen, Fed. Rep. of Germany

[73] Assignee: Chemische Werke Huels, AG, Fed. Rep. of Germany

[21] Appl. No.: 508,621

[22] Filed: Jun. 28, 1983

[30] Foreign Application Priority Data

Jul. 3, 1982 [DE] Fed. Rep. of Germany ....... 3224880

[51] Int. Cl.$^4$ .................. C07D 263/04; C07D 263/08
[52] U.S. Cl. ..................................... 548/239; 548/215
[58] Field of Search ................................ 548/239, 215

[56] References Cited

U.S. PATENT DOCUMENTS

3,813,378  5/1974  Witte et al. ..................... 548/239

FOREIGN PATENT DOCUMENTS

1086572  10/1967  United Kingdom .

Primary Examiner—Donald G. Daus
Assistant Examiner—S. A. Gibson
Attorney, Agent, or Firm—Millen & White

[57] ABSTRACT

For the preparation of pure, anhydrous cyclic imido esters, nitriles are reacted with amino alcohols with splitting off of ammonia at temperatures of 90°–230° C. under a pressure of 1.1–10 bar. The catalysts employed are metallic compounds. The process results in substantially shorter reaction times.

12 Claims, No Drawings

PROCESS FOR PREPARING ANHYDROUS CYCLIC IMIDO ESTERS

BACKGROUND OF THE INVENTION

Cyclic imido esters have been prepared by reacting nitriles with amino alcohols and driving off the resultant ammonia, at temperatures of between 50° and 180° C., as disclosed in, e.g., DOS No. 2,127,776, corresponding to U.S. Pat. No. 3,813,378, the disclosure of which is incorporated herein by reference. Suitable catalysts employed include metallic salts which are sufficiently dispersible in the reaction medium. In general, the reaction is carried out at atmospheric pressure. According to the aforementioned reference, it is possible to conduct the reaction under elevated or reduced pressure. However, the reference further teaches that operating under reduced pressure may be advantageous because the ammonia produced is thereby immediately removed from the reaction medium. However, one disadvantage in this process is the very long reaction time.

Therefore, a need still exists for an improved process which avoids the disadvantages of known processes.

OBJECTS OF THE INVENTION

One object of the present invention is to provide a process of producing cyclic imido esters in higher yields and with considerably shorter reaction times than in known processes.

Another object of the invention is to provide a process for producing anhydrous cyclic imido esters in very high purity.

Upon further study of the specification and appended claims, further objects and advantages of this invention will become apparent to those skilled in the art.

SUMMARY OF THE INVENTION

These and other objects of the invention are achieved by providing, in a process for preparing an anhydrous cyclic imido ester by reacting a nitrile with an amino alcohol in the presence of a metal compound as catalyst, and driving off resultant ammonia, the improvement comprising effecting the reaction at a temperature of 90°–230° C. and under a pressure of 1.1–10 bar.

DETAILED DISCUSSION

The reaction of nitriles with amino alcohols is quite general and results in the formation of cyclic imido esters and ammonia according to the following equation:

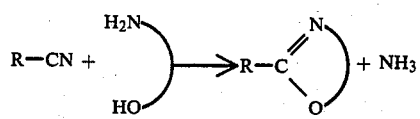

wherein R is any organic residue; and wherein the amine and hydroxyl groups are on suitable positions on an organic molecule such that a cyclic structure is possible for the resultant imido ester. Whenever a prior art process, effected at atmospheric pressure or reduced pressure, results in a cyclic imido ester, the present process, operating within the recited temperature and pressure ranges, will give improved results.

Contrary to the teaching in DOS No. 2,127,776, it has been found, surprisingly and unexpectedly, that the ammonia is removed immediately from the reaction medium within a specific pressure range of 1.1–10 bar, preferably 1.3–6 bar, especially 1.5–4 bar. It is particularly surprising that, in this pressure range according to the invention, the ammonia is split off more rapidly. Moreover, even with substantially shorter reaction times, at least the same or even considerably higher yields are attained. Even with greatly reduced catalyst concentrations, considerably higher yields are produced with substantially briefer reaction periods.

The reaction is effected at temperatures of 90°–230° C., preferably 120°–200° C. It will often be the case that the reflux temperature of the reaction mixture will fall within the recited temperature range at pressures within the recited range. In such cases, it will be advantageous to effect the reaction at reflux.

Any organic nitrile, including mononitriles, dinitriles or polynitriles, and any amino alcohol having properly disposed amine and hydroxyl groups can undergo condensation to a cyclic imido ester. In the case of a 1,2-substituted amino alcohol, the imido ester will be an oxazoline or an oxazole, depending on whether the reacting groups are on adjacent saturated or unsaturated carbon atoms.

The oxazolines can be polymerized to form poly(N-acyl ethylene imines), as disclosed, e.g., in DAS No. 1,206,585, corresponding to British Pat. No. 1,086,572.

Nitriles suitable for the process of this invention include, but are not limited to: alkylnitriles, e.g., acetonitrile, propionitrile, butyronitrile, isobutyronitrile and the like; arylnitriles, e.g., benzonitrile and the like; and dinitriles, e.g., adiponitrile and the like. Other suitable non-limitative nitriles are disclosed in U.S. Pat. No. 3,813,378.

Suitable amino alcohols include, but are not limited to: 1,2-substituted amino alcohols, having amine and hydroxyl groups on adjacent carbon atoms, e.g., 2-amino-ethanol, 2-amino-1-propanol, 1-amino-2-propanol and the like; and 1,3-substituted amino alcohols, e.g., 1-amino-3-propanol, 1-amino-3-butanol and the like. Other suitable non-limitative amino alcohols are disclosed in U.S. Pat. No. 3,813,378.

In general, 0.5–1.0 mole of amino alcohol is utilized per mole of nitrile or half mole (i.e., one molar equivalent) of dinitrile.

Compounds of lithium, copper, calcium, zinc, cadmium, manganese, iron, cobalt and/or nickel which are adequately soluble or finely dispersible in the reaction mixture are suitable as the catalysts, including, e.g., the oxides, halides, or carboxylates. The acetates are preferably employed. The amount of catalyst added is preferably about $10^{-5}$ to $10^{-1}$ mole per mole of nitrile.

The reaction is generally conducted without a solvent, but it is also possible to work with an inert solvent, e.g., chlorobenzene.

The process of this invention can be carried out continuously as well as discontinuously.

The mixture of nitrile, amino alcohol and catalyst, optionally with added inert solvent, is brought to the selected reaction pressure, preferably using an inert gas, e.g., nitrogen. The pressurized reaction mixture is then heated to the selected reaction temperature. Agitation can be provided by stirring and/or reflux. The reaction is preferably maintained in an inert atmosphere.

The reaction time is about 2–18 hours. Thus, the heretofore required reaction periods of 12 to 41 hours are greatly reduced. Despite the considerably briefer reaction times, substantially higher yields are generally obtained with the process of the present invention.

Compared to Example 14 of DOS No. 2,127,776, the present process with a substantially shorter reaction time (5 hours instead of 25 hours) achieves a relative increase in yield of 35%, the catalyst concentration in the present process being only about 2% of the concentration disclosed in the reference example.

The resultant cyclic imido esters are worked up in conventional fashion, generally by fractional distillation, which can be followed by further purification, e.g., by recrystallization. The products are anhydrous imido esters having a very high purity, generally about 99–99.9%.

The cyclic imido esters produced according to this invention can be utilized, for example, as corrosion protection agents, antistats, or selective solvents. They can also be polymerized in certain cases, e.g., to form poly(N-acyl ethylene imines).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example, all temperatures are set forth uncorrected in degrees Celsius; unless otherwise indicated, all parts and percentages are by weight.

EXAMPLES

20 Moles of the nitrile is brought to reaction pressure with 17.2 moles of the corresponding amino alcohol and 2 g (0.01 mole) of zinc acetate with the use of $N_2$ and heated to reflux. Distillation of the reaction solution results in pure, anhydrous ($\geq$99.5%) oxazolines. The results are shown below.

scope thereof, can make various changes and modifications of the invention to adapt it to various usages and conditions.

What is claimed is:

1. In a process for preparing an anhydrous cyclic imido ester by reacting a nitrile with an amino alcohol, in the presence of a metal compound as catalyst, and driving off resultant ammonia, the improvement comprising effecting the reaction at a temperature of 90°–230° C. and under a pressure of 1.1–10 bar.

2. A process according to claim 1, wherein said pressure is 1.3–6 bar.

3. A process according to claim 2, wherein said pressure is 1.5–4 bar.

4. A process according to claim 1, wherein said nitrile is acetonitrile, propionitrile, butyronitrile, isobutyronitrile, benzonitrile or adipodinitrile.

5. A process according to claim 1, wherein said amino alcohol is 2-aminoethanol, 2-amino-1-propanol, 1-amino-2-propanol, 1-amino-3-propanol, or 1-amino-3-butanol.

6. A process according to claim 1, wherein said amino alcohol is a 1,2-amino alcohol and said cyclic imido ester is an oxazoline.

7. A process according to claim 1, wherein said reaction temperature is 120°–200° C.

8. A process according to claim 1, wherein 0.5–1.0 mole of amino alcohol is reacted per molar equivalent of nitrile.

9. A process according to claim 1, wherein said catalyst is an oxide, halide or carboxylate of at least one of lithium, copper, calcium, zinc, cadmium, manganese, iron, cobalt or nickel.

10. A process according to claim 1, wherein the amount of catalyst is about $10^{-5}$ to $10^{-1}$ mole per molar equivalent of nitrile.

11. A process according to claim 1, wherein said reaction is effected at reflux.

12. A process according to claim 1, wherein the reaction temperature exceeds 180° C.

|   | Nitrile | Amine | Reaction Temp. (°C.) | Pressure (bar) | Time (h) | Conversion (Based on Nitrile) (%) | Yield (2) (%) |
|---|---|---|---|---|---|---|---|
| A | Propionitrile[1] | 2-Aminoethanol | 110 | 1.0 | 24 | 48 | 56 |
| 1 | Propionitrile | 2-Aminoethanol | 130 | 1.5 | 18 | 58 | 65 |
| 2 | Propionitrile | 2-Aminoethanol | 140 | 1.9 | 11 | 62 | 78 |
| 3 | Propionitrile | 2-Aminoethanol | 160 | 4.0 | 5 | 68 | 81 |
| 4 | Propionitrile | 1-Amino-2-propanol | 170 | 4.0 | 6 | 62 | 87 |
| 5 | Acetonitrile | 1-Amino-2-propanol | 165 | 4.0 | 6.5 | 53 | 75 |
| 6 | Acetonitrile | 2-Aminoethanol | 150 | 4.0 | 5.5 | 69 | 74 |
| 7 | Butyronitrile | 2-Aminoethanol | 190 | 4.0 | 7 | 67 | 67 |
| 8 | Benzonitrile | 2-Aminoethanol | 190 | 4.0 | 7 | 80 | 80 |

[1]Comparative Example
[2]Due to excess nitrile, the theoretical conversion is 86%.

The preceding example can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and